United States Patent
Kang et al.

(10) Patent No.: US 10,575,480 B2
(45) Date of Patent: Mar. 3, 2020

(54) METHOD FOR CULTIVATING COFFEE BEAN USING DEEP SEA WATER AND DEVELOPMENT OF HIGH QUALITY COFFEE USING THE SAME

(71) Applicant: KANGWON NATIONAL UNIVERSITY-INDUSTRY COOPERATION FOUNDATION, Gangwon-do (KR)

(72) Inventors: Won Hee Kang, Gangwon-do (KR); Cheon Seok Woo, Gangwon-do (KR); Do Hun Kim, Gangwon-do (KR)

(73) Assignee: KANGWON NATIONAL UNIVERSITY UNIVERSITY-INDUSTRY CORPORATION FOUNDATION, Gangwon-do (KR)

(*) Notice: Subject to any disclaimer, the term of this patent is extended or adjusted under 35 U.S.C. 154(b) by 140 days.

(21) Appl. No.: 15/826,995

(22) Filed: Nov. 30, 2017

(65) Prior Publication Data
US 2018/0359978 A1    Dec. 20, 2018

(30) Foreign Application Priority Data

Jun. 14, 2017 (KR) ................ 10-2017-0074843

(51) Int. Cl.
| | |
|---|---|
| *A01H 5/08* | (2018.01) |
| *A23L 33/105* | (2016.01) |
| *A23L 25/00* | (2016.01) |
| *A01C 21/00* | (2006.01) |
| *A23F 5/02* | (2006.01) |
| *A01H 6/76* | (2018.01) |
| *A01H 5/10* | (2018.01) |
| *A01G 22/00* | (2018.01) |
| *A01G 25/00* | (2006.01) |

(52) U.S. Cl.
CPC .............. *A01H 5/08* (2013.01); *A01C 21/00* (2013.01); *A01G 22/00* (2018.02); *A01H 5/10* (2013.01); *A01H 6/76* (2018.05); *A23F 5/02* (2013.01); *A23L 25/20* (2016.08); *A23L 33/105* (2016.08); *A01G 25/00* (2013.01); *A23V 2002/00* (2013.01)

(58) Field of Classification Search
CPC ........ A23L 33/105; A23L 25/20; A23L 33/00; A23G 22/00; A23G 22/40; A01H 5/08; A01H 5/10; A01C 21/00; A01G 25/00
USPC .......................................... 426/74, 629, 648
See application file for complete search history.

(56) References Cited

U.S. PATENT DOCUMENTS

2005/0229828 A1* 10/2005 Martin

FOREIGN PATENT DOCUMENTS

| CN | 104920149 | * | 9/2015 |
|---|---|---|---|
| KR | 10-2011-0054716 | | 5/2011 |
| KR | 10-2012-0022396 | | 3/2012 |
| WO | WO2015/116001 | * | 8/2015 |

* cited by examiner

*Primary Examiner* — Helen F Heggestad

(57) ABSTRACT

The present disclosure relates to a method for cultivating coffee bean with improved growth and contents of nutritional ingredients, including: (a) a step of preparing diluted deep sea water by mixing undiluted deep sea water with water; and (b) a step of irrigating coffee tree with the diluted deep sea water prepared in the step (a), coffee bean with improved growth and contents of nutritional ingredients, cultivated by the method, and a processed food using the coffee bean.

2 Claims, 6 Drawing Sheets

METHOD FOR CULTIVATING COFFEE BEAN USING DEEP SEA WATER AND DEVELOPMENT OF HIGH QUALITY COFFEE USING THE SAME

CROSS-REFERENCE TO RELATED APPLICATION

This application claims priority of Korean Patent Application No. 10-2017-0074843, filed on Jun. 14, 2017, in the KIPO (Korean Intellectual Property Office), the disclosure of which is incorporated herein entirely by reference.

BACKGROUND OF THE INVENTION

Field of the Invention

The present disclosure relates to a method for cultivating coffee bean with improved growth and contents of nutritional ingredients, including: (a) a step of preparing diluted deep sea water by mixing undiluted deep sea water with water; and (b) a step of irrigating coffee tree with the diluted deep sea water prepared in the step (a), coffee bean with improved growth and contents of nutritional ingredients, cultivated by the method, and a processed food using the coffee bean.

Description of the Related Art

Deep sea water is a clean sea water found in deep sea with a depth of 200 m or greater where sunlight cannot reach. Its temperature is stabilized at 2° C. or below throughout the year. In Korea, deep sea water upwelling from the North Pacific Ocean flows into the East Sea. The characteristics of the deep sea water are as follows. Firstly, the deep sea water is rich in nutrients, particularly inorganic nutrients necessary for plant growth such as nitrates, phosphates, silicates, etc., as compared to the surface water. Secondly, the deep sea water has an elemental composition similar to that of living organisms, contains most elements existing in the Earth, contains less degradable particulate or dissolved organic and suspending substances that aggravate water quality and contains less harmful artificial pollutants such as pathogens, bacteria, parasites, periphytons, environmental hormones, etc. Thirdly, the deep sea water has a lower temperature than the surface water throughout the year. Fourthly, the deep sea water is physically, chemically and biologically stable in water quality with less variation due to mineralization. Lastly, the deep sea water has resource characteristics such as low-temperature stability, cleanness, eutrophy, maturity, mineral balance, etc. Accordingly, the deep sea water having these characteristics has high resource values in various applications such as freshwater aquaculture, development of high-quality drinking water, extraction of high value-added substances, development of clean energy, fishery, production of useful materials, recovery of energy, etc. and can be seen as a clean, recyclable, large-scale resource without the concern of depletion.

Coffee belongs to the genus *Coffea* of the family Rubiaceae. Commercially cultivated three species are *arabica*, *robusta* (*canephora*) and *liberica*. Coffee is a representative drink with balanced bitter, astringent, sour and sweet tastes. It is the most popular drink in the world and its Korean market is also growing consistently with increased consumption in coffee shops and at home.

Coffee is known to have mental effects such as stimulating effect, mood change, and so on. Coffee is also known to reduce the risk of neurological diseases such as Alzheimer's disease, Parkinson's disease, and so on. Further, coffee is also known to reduce the risk of metabolic diseases caused by oxidative stress. Moderate amount of coffee intake provides several positive effects to normal adults except children and pregnant women. It is because coffee contains various physiologically active ingredients such as polyphenol compounds, tocopherols, as well as antioxidants such as chlorogenic acid, caffeine, melanoidin, etc.

Korean Patent Publication No. 10-2012-0022396, published on Mar. 12, 2012, discloses a method for cultivating vegetables with superior red color expression using deep sea water and Korean Patent Publication No. 10-2011-0054716, published on May 25, 2011, discloses a method for cultivating fruits using deep sea water. But, a method for cultivating coffee using deep sea water has never been reported.

SUMMARY OF THE INVENTION

The present disclosure is designed to solve the problems described above and is directed to establishing a method for cultivating coffee bean with improved growth and contents of nutritional ingredients by irrigating coffee tree with an optimum concentration of deep sea water to improve growth and contents of nutritional ingredients as compared to the coffee bean cultivated without the irrigation or by irrigating with deep sea water of different concentrations.

In order to solve the problems described above, the present disclosure provides a method for cultivating coffee bean with improved growth and contents of nutritional ingredients, including: (a) a step of preparing diluted deep sea water by mixing undiluted deep sea water with water; and (b) a step of irrigating coffee tree with the diluted deep sea water prepared in the step (a).

The present disclosure also provides coffee bean with improved growth and contents of nutritional ingredients cultivated by the method.

The present disclosure also provides a processed food using the coffee bean with improved growth and contents of nutritional ingredients.

Coffee bean cultivated by irrigating with deep sea water of a specific concentration according to the present disclosure shows improved growth and improved contents of nutritional ingredients such as calcium and iron as compared to the coffee bean cultivated without the irrigation or by irrigating with deep sea water of different concentrations. Accordingly, increased income may be expected for coffee farmers and high-quality coffee may be provided for consumers.

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

Figure 1:
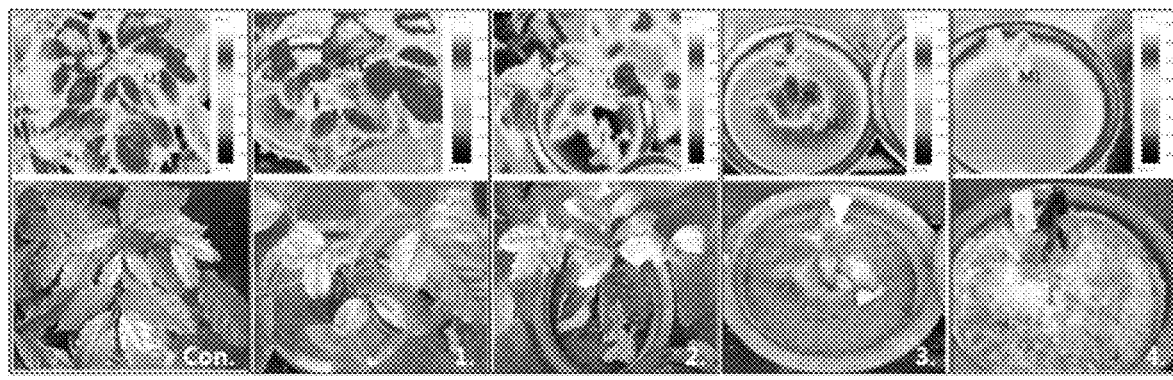
FIG. 1 compares the images of coffee seedlings cultivated by treating with deep sea water of different concentrations for 3 months, taken with a thermal imaging camera and a normal camera. Con: not treated with deep sea water, 1: treated with 5% deep sea water, 2: treated with 10% deep sea water, 3: treated with 20% deep sea water, 4: treated with 40% deep sea water.

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

Reference herein to a layer formed "on" a substrate or other layer refers to a layer formed directly on top of the substrate or other layer or to an intermediate layer or intermediate layers formed on the substrate or other layer. It will also be understood by those skilled in the art that structures or shapes that are "adjacent" to other structures or shapes may have portions that overlap or are disposed below the adjacent features.

In this specification, the relative terms, such as "below", "above", "upper", "lower", "horizontal", and "vertical", may be used to describe the relationship of one component, layer, or region to another component, layer, or region, as shown in the accompanying drawings. It is to be understood that these terms are intended to encompass not only the directions indicated in the figures, but also the other directions of the elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

In order to achieve the objects of the present disclosure, the present disclosure provides a method for cultivating coffee bean with improved growth and contents of nutritional ingredients, including: (a) a step of preparing diluted deep sea water by mixing undiluted deep sea water with water; and (b) a step of irrigating coffee tree with the diluted deep sea water prepared in the step (a).

In the method for cultivating coffee bean of the present disclosure, the diluted deep sea water may be specifically 2-6% (v/v) diluted deep sea water, more specifically 2.5-5% (v/v) diluted deep sea water. When coffee is cultivated with diluted deep sea water of the above-described concentration, the size and weight of coffee bean can be increased and the contents of nutritional ingredients such as calcium and iron in the coffee bean can be maximized without affecting the growth of coffee tree.

Also, in the method for cultivating coffee bean of the present disclosure, the irrigation may be performed with specifically 2- to 4-day intervals, more specifically 3- to 3.5-day intervals, although not being limited thereto.

Also, in the method for cultivating coffee bean of the present disclosure, the nutritional ingredient may be one or more selected from a group consisting of calcium and iron, although not being limited thereto.

More specifically, the method for cultivating coffee bean of the present disclosure may include: (a) a step of preparing 2-6% (v/v) diluted deep sea water by mixing undiluted deep sea water with water; and (b) a step of irrigating coffee tree with the diluted deep sea water prepared in the step (a) with 2- to 4-day intervals.

More specifically, it may include: (a) a step of preparing 2.5-5% (v/v) diluted deep sea water by mixing undiluted deep sea water with water; and (b) a step of irrigating coffee tree with the diluted deep sea water prepared in the step (a) with 3- to 3.5-day intervals.

The present disclosure also provides coffee bean with improved growth and contents of nutritional ingredients cultivated by the above-described method.

The present disclosure also provides a processed food using the coffee bean with improved growth and contents of nutritional ingredients. The processed food is not specially limited in its kind. For example, the processed food may be coffee, meat, sausage, bread, chocolate, candy, snack, confectionery, pizza, instant noodle, other noodles, gum, dairy products including ice cream, soup, beverage, tea, drink, alcoholic beverage, vitamin complex, etc. and includes all processed foods in ordinary contexts.

Hereinafter, the present disclosure is described in detail through examples. However, the following examples only illustrate the present disclosure and the present disclosure is not limited to the examples.

Example 1: Preparation of East Sea Diluted Deep Sea Water

The general characteristics of East Sea deep sea water used in the present disclosure are described in Table 1. The deep sea water used in the present disclosure is characterized by high dissolved oxygen, less organic matter and less microorganisms. 2.5%, 5%, 10%, 20% and 40% diluted deep sea water were prepared by mixing the East Sea deep sea water with 40-, 20-, 10-, 5- and 2.5-fold distilled water.

TABLE 1

General characteristics of East Sea deep sea water (mg/L)

| | General sea water | East Sea deep sea water (Goseong) | | General sea water | East Sea deep sea water (Goseong) |
|---|---|---|---|---|---|
| Cadmium | 0.00005 | <0.0005 | Calcium | 4.22 | 4.22 |
| Lead | 0.00003 | 0.002 | Magnesium | 1326 | 1326 |
| Arsenic | 0.0023 | 0.010 | Aluminum | 0.005 | 0.0015 |
| Mercury | 0.00005 | — | Cobalt | 0.0008 | 0.0001-0.00028 |
| Selenium | 0.00045 | 0.057 | Copper | 0.003 | 0.001-0.003 |
| Fluorine | 1.3 | 0.3 | Nickel | 0.002 | 0.003-0.005 |
| Nitrate nitrogen | 0.5 | 0.4 | Chromium | 0.0006 | 0.0004 |
| Nitrite nitrogen | — | <0.001 | Vanadium | 0.0015 | 0.0181 |
| Total cyanide | — | — | Manganese | 0.002 | 0.002 |
| Chromium(VI) | 0.0006 | — | Zinc | 0.005 | 0.005-0.020 |
| Boron | 4.4 | 4.4 | Molybdenum | 0.01 | 0.0001 |
| Bromine | 67.3 | 67.3 | Iron | 0.03 | 0.0965 |
| Dissolved oxygen | — | 6.59 | Rubidium | 0.12 | — |
| Chemical oxygen demand | — | 0.2 | Argon | 0.45 | — |
| General bacteria (MPN/100 mL) | — | <3.0 | Uranium | 0.003 | 0.001-0.003 |
| pH | 8.0 | 7.82 | Sulfate | 928 | 928 |
| Total nitrogen | 0.5 | 0.45 | Bicarbonate | 28 | 28 |
| Total phosphorus | 0.07 | 0.03 | Urea ion | 0.06 | 0.06 |
| Ammonia nitrogen | — | 0.04 | Total organic carbon | 3.1 | — |
| Phosphate phosphorus | 0.218 | 0.2 | Soluble silicon | 1 | 1.34 |
| Chloride | 19.870 | 19.870 | Barium | 0.03 | 0.006 |
| Sodium | 11.050 | 11.050 | Lithium | 0.18 | 0.04-0.18 |
| Potassium | 416 | 416 | Strontium | 8.1 | 2.234-7.96 |

Example 2: Growth and Physiological Characterization of Coffee Seedling Cultivated Using Deep Sea Water Experiment was conducted from March to July in 2016 on coffee seedlings grown in a greenhouse in Kangwon National University. Uniform coffee seedlings were selected and planted in black pots with a diameter of 18 cm. Loam soil and humic soil (2:1) were used as soil and 0%, 5%, 10%, 20% or 40% deep sea water was irrigated to each pot for 2 months, twice a week and 330 mL per each. The greenhouse was maintained at a temperature of 15-24° C.

(1) Growth of Coffee Seedling

The growth of coffee seedlings (height, stem thickness, leaf length and leaf width) was investigated on days 15, 30, 45 and 60 after the planting. As a result, the height showed no statistical difference significant in all groups. But, for the stem thickness, leaf length and leaf width, the 20% and 40% deep sea water groups showed retarded growth on day 60. In contrast, the 5% and 10% deep sea water groups showed no significant difference in growth from a control group.

TABLE 2

Growth of coffee seedling cultivated using deep sea water

| Day | Control | 5% DSW | 10% DSW | 20% DSW | 40% DSW |
|---|---|---|---|---|---|
| | | | Height (cm) | | |
| 15 | $10.33^{az}$ | $10.00^a$ | $10.33^a$ | $10.83^a$ | $12.23^a$ |
| 30 | $11.30^a$ | $10.47^a$ | $11.33^a$ | $11.67^a$ | $13.93^a$ |

TABLE 2-continued

Growth of coffee seedling cultivated using deep sea water

| Day | Control | 5% DSW | 10% DSW | 20% DSW | 40% DSW |
|---|---|---|---|---|---|
| 45 | 12.17$^a$ | 12.10$^a$ | 11.93$^a$ | 12.33$^a$ | 14.17$^a$ |
| 60 | 16.33$^a$ | 15.57$^a$ | 14.33$^a$ | 13.63$^a$ | 14.67$^a$ |
| Stem thickness (mm) | | | | | |
| 15 | 3.24$^a$ | 2.51$^a$ | 2.62$^a$ | 2.52$^a$ | 2.33$^a$ |
| 30 | 3.49$^a$ | 2.70$^a$ | 2.88$^a$ | 2.59$^a$ | 2.78$^a$ |
| 45 | 3.74$^a$ | 2.99$^a$ | 3.06$^a$ | 2.76$^a$ | 2.87$^a$ |
| 60 | 4.15$^a$ | 3.30$^{ab}$ | 3.31$^{ab}$ | 2.88$^b$ | 2.86$^b$ |
| Leaf length (cm) | | | | | |
| 15 | 6.47$^a$ | 5.73$^a$ | 4.63$^{ab}$ | 2.87$^b$ | 2.77$^b$ |
| 30 | 8.47$^a$ | 7.73$^{ab}$ | 7.40$^{ab}$ | 4.97$^b$ | 4.87$^b$ |
| 45 | 10.67$^a$ | 11.03$^a$ | 9.77$^a$ | 8.17$^a$ | 8.53$^a$ |
| 60 | 15.00$^a$ | 14.90$^a$ | 13.97$^{ab}$ | 10.73$^{bc}$ | 7.83$^c$ |
| Leaf width (cm) | | | | | |
| 15 | 2.50$^a$ | 1.92$^{ab}$ | 1.47$^{ab}$ | 1.33$^b$ | 1.37$^b$ |
| 30 | 4.37$^a$ | 3.37$^{ab}$ | 2.93$^{ab}$ | 2.53$^b$ | 2.33$^b$ |
| 45 | 4.13$^a$ | 3.87$^a$ | 3.63$^a$ | 3.10$^a$ | 3.03$^a$ |
| 60 | 6.30$^a$ | 5.67$^a$ | 5.37$^a$ | 4.03$^b$ | 2.83$^b$ |

(2) Comparison of Growth of Coffee Seedling Using Thermal Imaging Camera

After cultivating coffee seedlings for 3 months using deep sea water, images were taken using a thermal imaging camera and a normal camera. As a result, it was found out that the coffee seedlings could not grow when the 40% deep sea water was used and the growth of the seedlings was also unsatisfactory when the coffee was cultivated using the 20% deep sea water. Accordingly, it was confirmed that 5-10% deep sea water is suitable for cultivation of coffee as shown in FIG. 1.

Example 3: Growth and Physiological Characterization of Coffee Leaf Cultivated Using Deep Sea Water (1) Chlorophyll Content of Coffee Leaf The chlorophyll content of coffee leaves treated with deep sea water of different concentrations was investigated on day 75 after the planting at different times (morning, daytime and evening). It was found out that the coffee leaves cultivated using deep sea water showed higher chlorophyll content than the coffee leaves not treated with deep sea water (control) as shown in Table 3. However, the chlorophyll content could not be measured for the coffee cultivated using the 40% deep sea water because the seedlings could not grow.

(2) Electrical Conductivity of Coffee

After harvesting coffee leaves treated with deep sea water of different concentrations, relative electrical conductivity was investigated as a response to salts in the deep sea water from among physiological responses to the deep sea water. After punching leaf disks (3 per each) with a diameter of 3 cm and shaking after adding 15 mL of distilled water, the leaves were left alone at room temperature for 12 hours. After measuring initial electrical conductivity (S1), the solution was heated to 100° C. for 15 minutes and then cooled to room temperature. Then, the final electrical conductivity (S2) was measured using an EC meter (Mettler-Toledo GmbH 8603, Schwerzenbach, Switzerland). The relative electrical conductivity (REC) of the coffee leaves treated with deep sea water of different concentrations was calculated according to the following equation.

REC (%)=$S1/S2 \times 100$

Figure 2:
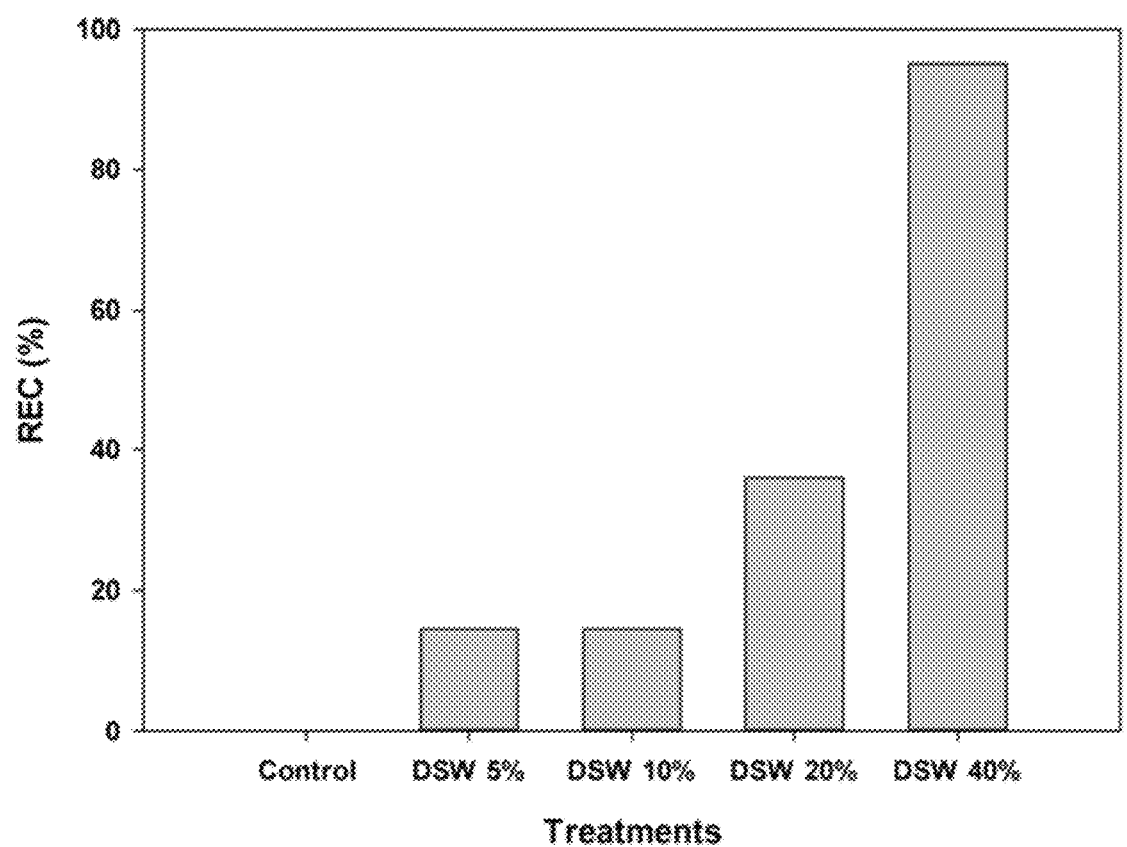
FIG. 2 compares the REC (relative electrical conductivity) of coffee leaves cultivated by treating with deep sea water of different concentrations. Control: not treated with deep sea water, DSW: deep sea water.

As a result, the REC was higher for the 20% and 40% deep sea water with 36% and 95.2%, respectively, than the 5% and 10% deep sea water with 14.5% as shown in FIG. 2.

(3) Measurement of Relative Water Content of Coffee Leaf

After harvesting coffee leaves treated with deep sea water of different concentrations, relative water content (RWC) was calculated according to the following equation.

RWC (%)=$((FW-DW)/(TW-DW)) \times 100$

FW: fresh weight, TW: turgid weight, DW: dry weight.

Figure 3:
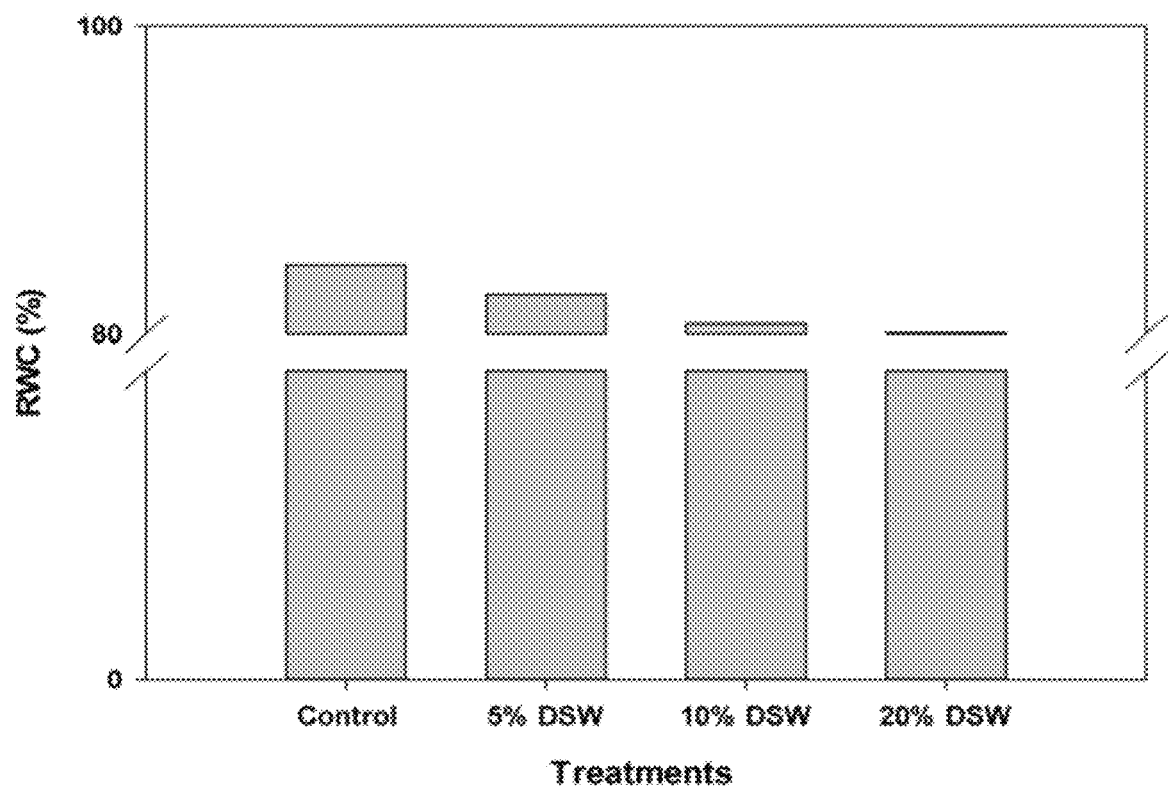
FIG. 3 compares the RWC (relative water content) of coffee leaves cultivated by treating with deep sea water of different concentrations. Control: not treated with deep sea water, DSW: deep sea water.

As a result, the RWC was the highest for the control group with 84.5%. The groups treated with 5% and 10% deep sea water showed recoverable wilting with a difference of about 2-3% from the control group, whereas the groups treated with 20% and 40% deep sea water showed irrecoverable wilting with a difference of 3% or greater from the control group as shown in FIG. 3.

(4) Observation of Pores of Coffee Leaf Cultivated Using Deep Sea Water

The leaves of coffee tree cultivated using deep sea water of different concentrations were harvested and their pores were observed under a microscope. The number, length and width of the pores were compared.

TABLE 4

Observation of pores of coffee leaf cultivated using deep sea water

| Treatment condition | Pore length (μm) | Pore width (μm) | Pore number (/mm$^2$) |
|---|---|---|---|
| Control | 20.9$^a$ | 17.1$^a$ | 179$^a$ |
| 5% DSW | 20.3$^{ab}$ | 16.6$^{ab}$ | 179$^{ab}$ |

TABLE 3

Chlorophyll content in coffee leaf cultivated using deep sea water

| | Measurement time | | | | | | | | |
|---|---|---|---|---|---|---|---|---|---|
| | 9:00 (am) | | | 1:00 (pm) | | | 5:00 (pm) | | |
| Treatment condition | Upper leaf | Lower leaf | Mean | Upper leaf | Lower leaf | Mean | Upper leaf | Lower leaf | Mean |
| Control | 40.00$^{bz}$ | 60.70$^a$ | 51.68$^b$ | 41.43$^b$ | 63.37$^a$ | 52.40$^b$ | 42.77$^b$ | 64.57$^a$ | 53.67$^b$ |
| 5% DSW | 45.60$^{ab}$ | 67.20$^a$ | 56.40$^{ab}$ | 50.63$^a$ | 64.67$^a$ | 57.65$^a$ | 50.30$^a$ | 65.60$^a$ | 57.95$^a$ |
| 10% DSW | 50.00$^a$ | 64.90$^a$ | 57.45$^a$ | 50.53$^a$ | 62.60$^a$ | 56.57$^{ab}$ | 50.80$^a$ | 69.03$^a$ | 59.92$^a$ |
| 20% DSW | 48.13$^a$ | 60.87$^a$ | 54.50$^{ab}$ | 51.50$^a$ | 64.60$^a$ | 58.05$^a$ | 52.70$^a$ | 64.70$^a$ | 58.70$^a$ |
| 40% DSW | — | — | — | — | — | — | — | — | — |

TABLE 4-continued

Observation of pores of coffee leaf cultivated using deep sea water

| Treatment condition | Pore length (μm) | Pore width (μm) | Pore number (/mm²) |
|---|---|---|---|
| 10% DSW | 20.2$^{ab}$ | 16.1$^{bc}$ | 168$^{abc}$ |
| 20% DSW | 19.2$^{bc}$ | 15.9$^{c}$ | 162$^{bc}$ |
| 40% DSW | 18.8$^{c}$ | 15.4$^{c}$ | 160$^{c}$ |

As a result, the number, length and width of the pores decreased as the concentration of the deep sea water was increased. Because the coffee leaves treated with 5% deep sea water showed no significant difference from the control group, it is thought that 5% deep sea water is suitable for cultivation of coffee.

Example 4: Investigation of Soil Composition after Treatment with Deep Sea Water After the treatment with deep sea water of different concentrations, soil remaining in each pot was subjected to analysis. 3 soil samples per each group were analyzed at the soil laboratory of the Gangneung City Agricultural Development & Technology Center. Measurement was made as follows.

Acidity (pH): EC meter, organic matter content: Tyurin's method, phosphate (available phosphate) content: Lancaster's method, cation content: 1 N ammonium acetate leaching (ICP-AES), lime requirement: ORD method.

TABLE 5

Analysis of soil composition

| DSW conc. (%) | pH (1:5) | OM (g/kg) | P (mg/kg) | K (cmol+/kg) | Ca (cmol+/kg) | Mg (cmol+/kg) | EC (dS/m) |
|---|---|---|---|---|---|---|---|
| 40% | 5.67$^{az}$ | 23.3$^{a}$ | 2,347.3$^{b}$ | 5.43$^{a}$ | 3.43$^{a}$ | 3.50$^{a}$ | 8.97$^{a}$ |
| 20% | 5.87$^{a}$ | 13.0$^{a}$ | 2,502.7$^{ab}$ | 5.25$^{a}$ | 3.27$^{a}$ | 3.23$^{a}$ | 7.77$^{ab}$ |
| 10% | 5.97$^{a}$ | 15.0$^{a}$ | 2,621.3$^{ab}$ | 6.07$^{a}$ | 3.90$^{a}$ | 3.20$^{a}$ | 7.07$^{ab}$ |
| 5% | 5.70$^{a}$ | 20.0$^{a}$ | 2,875.0$^{a}$ | 6.12$^{a}$ | 3.50$^{a}$ | 2.90$^{a}$ | 5.10$^{b}$ |
| Control | 5.80$^{a}$ | 21.3$^{a}$ | 2,819.3$^{a}$ | 6.65$^{a}$ | 3.73$^{a}$ | 2.43$^{a}$ | 2.00$^{c}$ |

As a result, although the groups treated with deep sea water showed largely similar soil composition to the control group, the groups treated with 10-40% deep sea water showed slightly higher EC values.

Example 5: Establishment of Coffee Tree Cultivation Environment Using Deep Sea Water (1) Establishment of Greenhouse Studies on coffee bean production using deep sea water were conducted in a greenhouse of about 450 m² at Kangwon National University. The greenhouse was comparted into 3 sections with a size of 7 m×25 m each. Loam soil with good water drainage and water retention at the same time was used. A ventilation system was installed in the greenhouse for uniform air circulation and white and black covers were used to control sunlight intensity and protect the coffee tree from strong sunlight. A pump was used for irrigation.

The coffee greenhouse was designed as other greenhouses. In order to prevent heat loss, a greenhouse was installed inside a large greenhouse to provide a good environment for the growth of coffee tree. The coffee trees were planted in the 3 sections, with 3-4 rows per each section. The spacing between the trees was 2 m and the spacing between the rows was 2.5 m. 70 coffee trees were planted in one section and a total of 210 trees were planted in the 3 sections. In addition, coffee seedlings were planted in 300 small pots.

(2) Maintenance of Optimal Growth Temperature

Temperature is the most important factor in the growth of coffee tree. The ideal growth temperature for *arabica* coffee is 15-24° C. Because the winter in Kangwondo is too cold for the growth of coffee, the temperature in the greenhouse was maintained at 10-12° C. at night and 18-22° C. during the day using a stove burning sawdust and kerosene. Also, rice straw was piled on the outer wall of the greenhouse to prevent heat loss.

(3) Supply of Water and Fertilizer

Water is very important in the cultivation of coffee tree. 6 L of water was supplied to each tress with 3-day intervals. As fertilizers, N, P and K necessary for plant growth were supplied using an irrigation system once a month. The supply amounts of N, P and K were 46-50 mL, 20 mL and 50 mL per tree, respectively. In addition, Poly-Feed dissolved in water was irrigated to the tree and adequate amounts nutrients and fertilizers helpful for tree growth were supplied if necessary.

(4) Pruning

Pruning is necessary to keep the coffee tree strong and healthy and to obtain a lot of coffee beans because the tree becomes weak if its branches grow in all directions. Pruning was performed to maintain the tree height at 1.7 m and buds growing above 1.7 m were removed immediately. Suckers and old branches were removed by the pruning. In order to prevent the coffee tree from falling and to protect the coffee tree during the fruiting season, each tree was supported by metal rods. A black plastic mulch was used to ensure the growth of the coffee tree and to reduce weed growth. Also, the space around the coffee tree was covered with wood chips and fallen leaves.

Example 6: Growth of Coffee Bean Cultivated Using Deep Sea Water

The difference in the growth of coffee beans cultivated using deep sea water of different concentrations was compared to determine the concentration of deep sea water for improving coffee production. Based on the result of preliminary experiment, 5% and 10% deep sea water were prepared.

Figure 4:
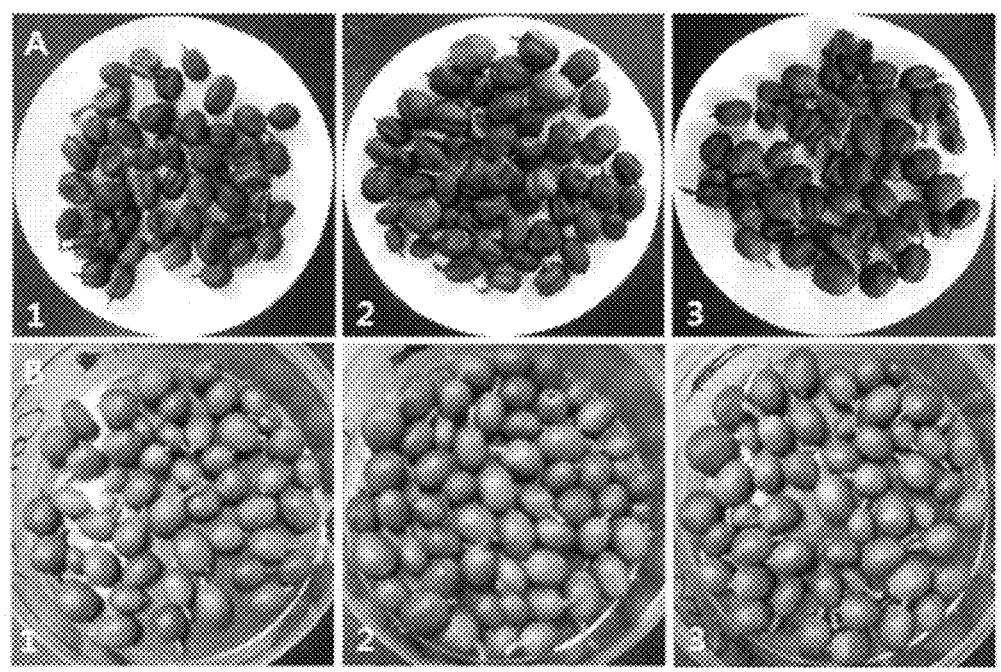
FIG. 4 compares the images of coffee beans cultivated by treating with deep sea water of different concentrations, after drying at 60° C. for 1 day (B) and drying at 60° C. for 7 days (A). 1: not treated with deep sea water, 2: treated with 5% deep sea water, 3: treated with 10% deep sea water.
Figure 5:
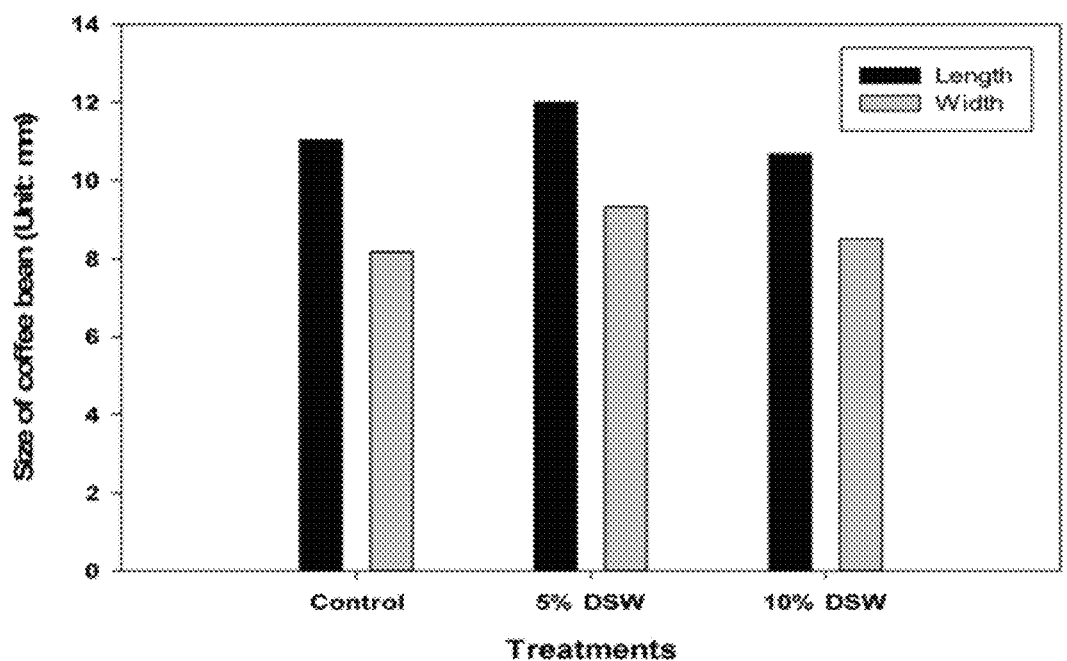
FIG. 5 compares the length and width of coffee beans cultivated by treating with deep sea water of different concentrations, after drying at 60° C. for 1 day. Control: not treated with deep sea water, DSW: deep sea water.
Figure 6:
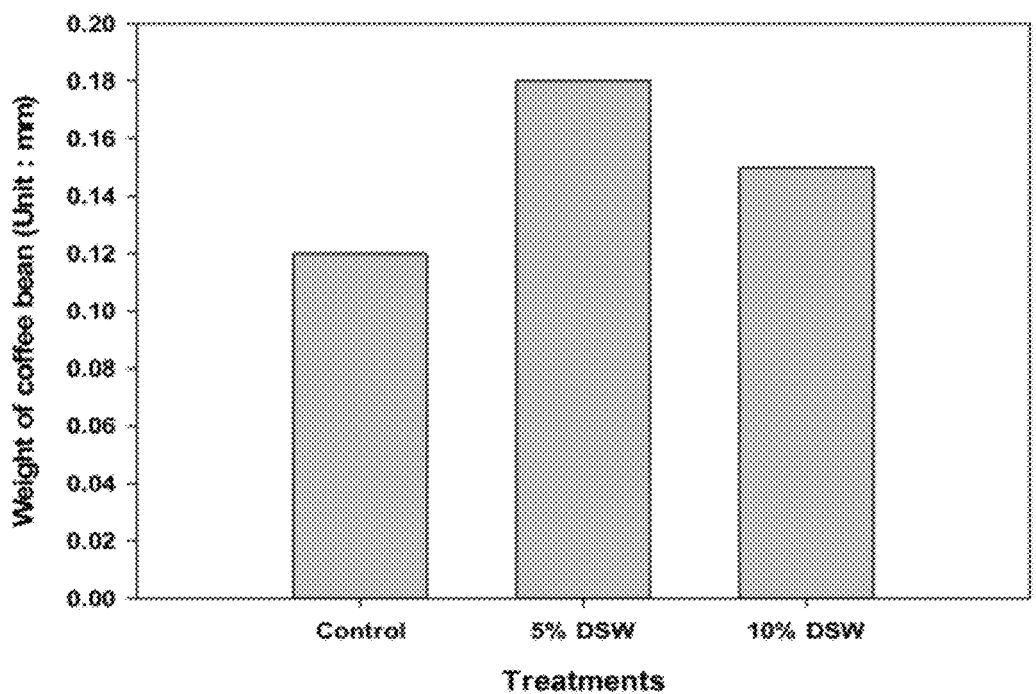
FIG. 6 compares the weight of coffee beans cultivated by treating with deep sea water of different concentrations, after drying at 60° C. for 1 day. Control: not treated with deep sea water, DSW: deep sea water.

Coffee tree was treated with 5% and 10% deep sea water after flowering in June to August. Then, coffee bean was sampled from each group firstly on Nov. 24, 2016 and then secondly on Jan. 9, 2017 and fresh weight, dry weight and size were compared While the coffee bean was formed during the summer after fertilization, the coffee tree was treated with deep sea water of different concentrations (control, 5%, 10%). After the first sampling, the group treated with 5% deep sea water showed the best result in size and weight than other groups. The 10% deep sea water group and the control group were similar in size, but the weight was larger for the coffee bean of the 10% deep sea water group than the control group as shown in FIGS. 4-6.

Figure 7:
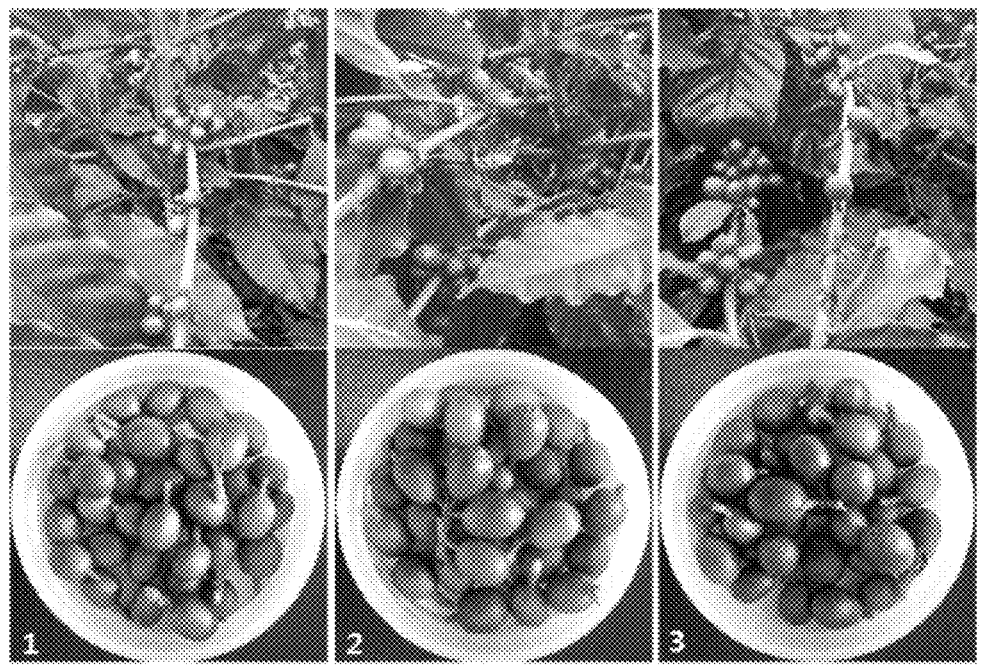
FIG. 7 compares the size of coffee beans cultivated by treating with deep sea water of different concentrations, after drying at 60° C. for 1 day. 1: not treated with deep sea water, 2: treated with 5% deep sea water, 3: treated with 10% deep sea water.
Figure 8:
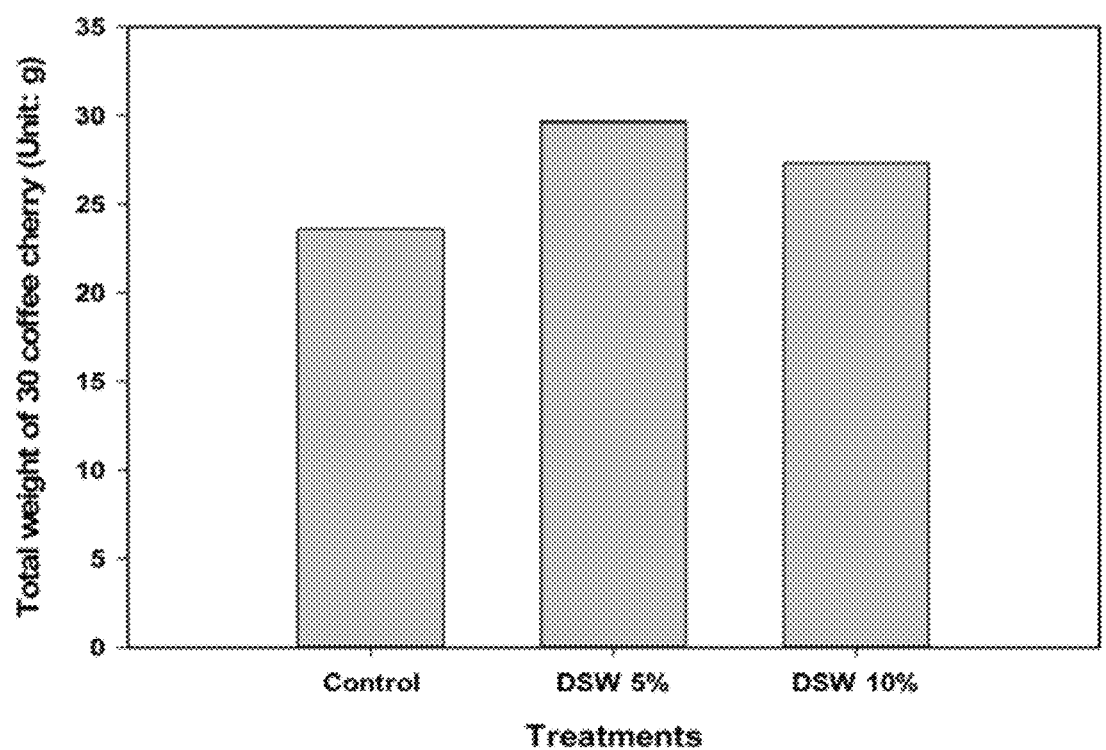
FIG. 8 compares the weight of coffee beans cultivated by treating with deep sea water of different concentrations. Control: not treated with deep sea water, DSW: deep sea water.
Figure 9:
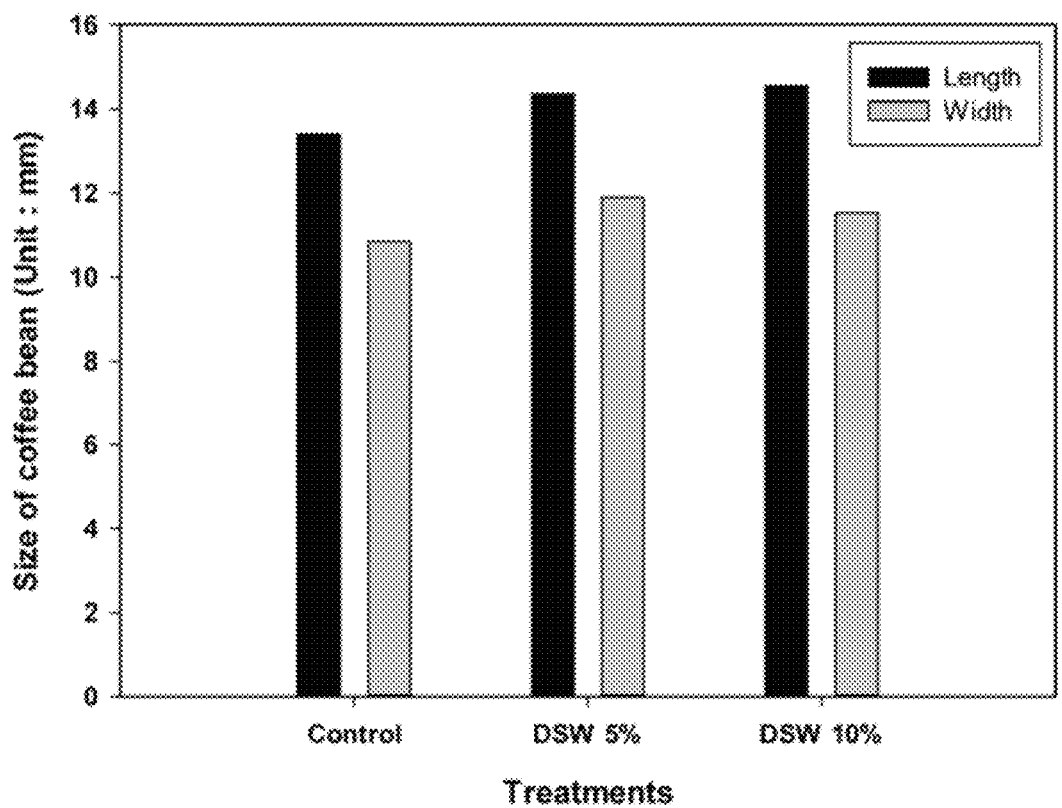
FIG. 9 compares the length and width of coffee beans cultivated by treating with deep sea water of different concentrations. Control: not treated with deep sea water, DSW: deep sea water.

The fresh weight of the 30 second samples harvested on Jan. 9, 2017 was 23.59 g for the control group, 29.65 g for the 5% deep sea water and 27.32 g for the 10% deep sea water group. That is to say, the fresh weight was the highest for the 5% group. When the size of the coffee beans was compared after the second harvesting, the size of the coffee beans of the 5% and 10% groups was much larger than that of the control group. The 5% group showed a larger size than the 10% group as shown in FIGS. 7-9.

Figure 10:
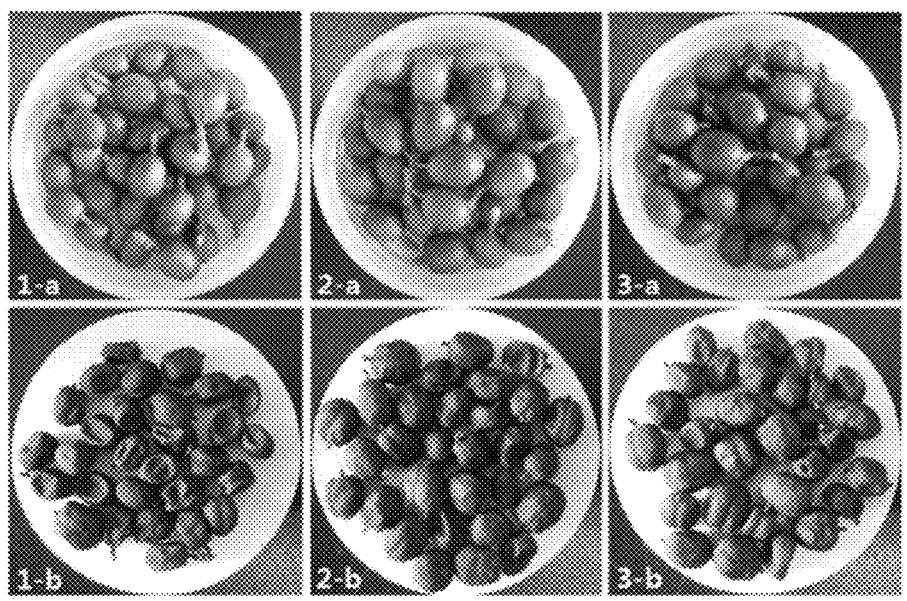
FIG. 10 compares coffee beans cultivated by treating with deep sea water of different concentrations, as harvested (a) and after drying (b). 1: not treated with deep sea water, 2: treated with 5% deep sea water, 3: treated with 10% deep sea water.
Figure 11:
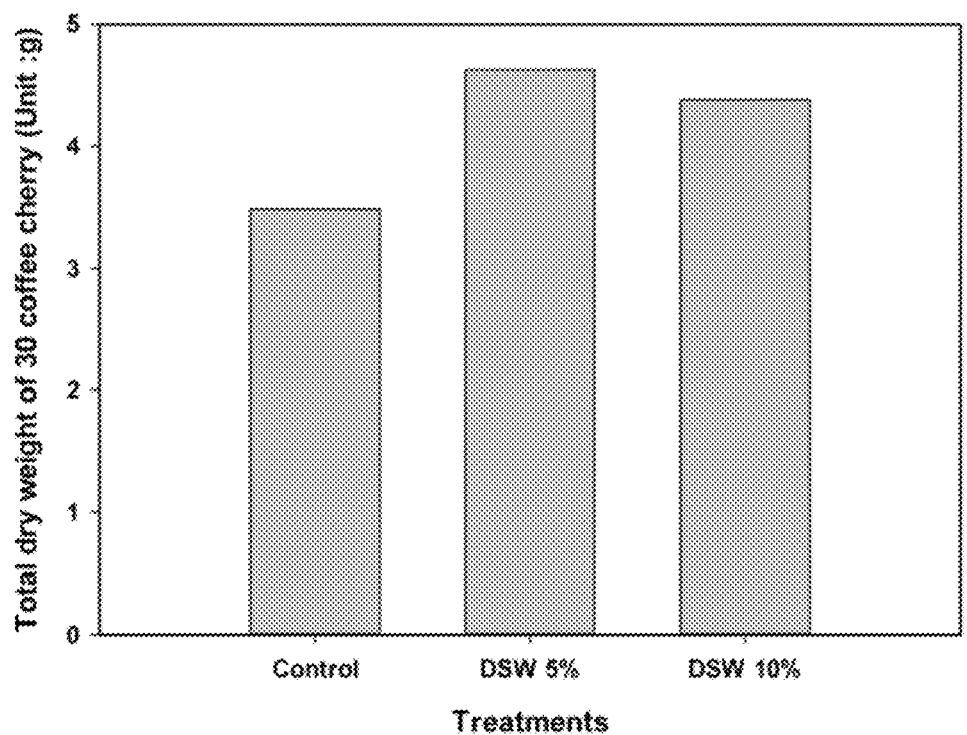
FIG. 11 compares the weight of coffee beans cultivated by treating with deep sea water of different concentrations, after drying. Control: not treated with deep sea water, DSW: deep sea water.
Figure 12:
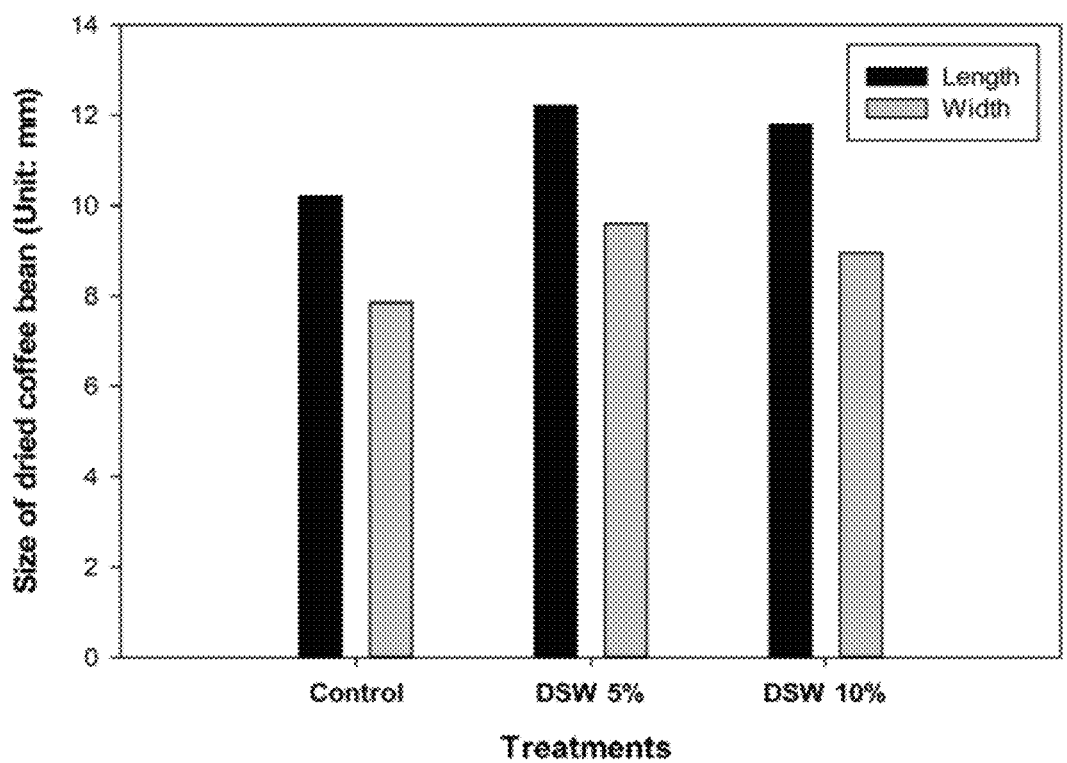
FIG. 12 compares the length and width of coffee beans cultivated by treating with deep sea water of different concentrations, after drying. Control: not treated with deep sea water, DSW: deep sea water.

The 30 second samples harvested on Jan. 9, 2017 were dried at 60° C. for 7 days and their weight was measured (control group: 3.49 g, 5% deep sea water group: 4.63 g, 10% deep sea water group: 4.38 g). The 5% deep sea water group showed the highest dry weight. Also, the dried coffee beans treated with 5% deep sea water showed the largest size as shown in FIGS. 10-12.

In conclusion, the coffee beans treated with deep sea water showed larger size, fresh weight and dry weight than the control group. Particularly, the size and weight of coffee bean could be increased best when it was cultivated using 5% deep sea water.

Example 7: Comparison of Nutritional Ingredients of Coffee Bean Cultivated Using Deep Sea Water A result of comparing nutritional ingredients contained in the coffee beans cultivated using deep sea water of different concentrations is shown in Table 6. The coffee beans cultivated using deep sea water showed higher protein, calcium and iron contents than the coffee bean without using deep sea water (control). The calcium and iron contents of coffee bean were the highest when it was cultivated using 2.5-5% deep sea water. And, the coffee bean cultivated using 2.5-5% deep sea water showed a lower sodium content than the control group.

TABLE 6

Comparison of nutritional ingredients of coffee bean cultivated using deep sea water

| Ingredients | Unit | Treatment condition | | | | |
| --- | --- | --- | --- | --- | --- | --- |
| | | Control | 2.5% DSW | 5% DSW | 10% DSW | 20% DSW |
| Water | kcal/100 g | 7.8 | 8.9 | 8.6 | 7.7 | 7.2 |
| Ash | g/100 g | 3.4 | 3.4 | 3.5 | 3.4 | 3.3 |
| Carbohydrate | g/100 g | 75.9 | 73 | 72.8 | 75.4 | 76.7 |
| Protein | g/100 g | 11 | 13.4 | 13.9 | 11.2 | 11 |
| Fat | g/100 g | 1.9 | 1.3 | 1.2 | 2.3 | 1.8 |
| Vitamin $B_2$ | mg/100 g | 0.1 | 0 | 0.1 | 0 | 0.1 |
| Vitamin $B_6$ | mg/100 g | 0 | 0 | 0 | 0 | 0 |
| Vitamin C | mg/100 g | 0 | 0 | 0 | 0 | 0 |
| Calcium | mg/100 g | 72.7 | 122.2 | 120.3 | 97.8 | 97.6 |
| Potassium | mg/100 g | 2353 | 2571 | 2572 | 2748 | 2669 |
| Iron | mg/100 g | 1.8 | 3.0 | 2.4 | 2.0 | 2.2 |

Example 8: Sensory Test of Coffee Bean Cultivated Using Deep Sea Water

Coffee beans cultivated using deep sea water according to the present disclosure were roasted. The roasted coffee beans were ground and sensory test was conducted after extracting coffee through hand drip by adding purified water. 30 Kangwon National University students were asked to score flavor, taste and overall preference based on 5-point scales (1: very poor, 2: poor, 3: moderate, 4: good, 5: very good). The result is given in Table 7. Bitterness was scored as follows: 1: almost nonexistent, 3: moderate, 5: strong.

As a comparative example, coffee beans cultivated without using deep sea were roasted and ground. Then, coffee was extracted through hand drip by adding 5% deep sea water.

TABLE 7

| | Sensory test | | | |
| --- | --- | --- | --- | --- |
| | Flavor | Taste | Bitterness | Overall preference |
| Control | 4.26 | 4.10 | 2.62 | 4.18 |
| Comparative example | 4.30 | 4.36 | 2.38 | 4.20 |
| 5% DSW | 4.52 | 4.60 | 1.80 | 4.68 |
| 10% DSW | 4.44 | 4.46 | 2.18 | 4.32 |

As can be seen from Table 7, the coffee prepared from the coffee bean cultivated using 5% deep sea water showed the best scores in flavor, taste and overall preference and the coffee prepared from the coffee bean cultivated without using deep sea of the control group showed the lowest scores. Also, the coffee prepared from the coffee bean cultivated using 5% deep sea water showed the lowest score in bitterness, meaning that the bitter taste is weak.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. A method for cultivating coffee bean tree, the method comprising:
    (a) a step of preparing diluted deep sea water by mixing undiluted deep sea water with water; and
    (b) a step of irrigating the coffee bean tree with the diluted deep sea water prepared in the step (a), wherein the method induces the coffee bean tree to produce larger and weightier beans which include more nutritional ingredients, wherein the nutritional ingredients are one or more selected from a group consisting of calcium and iron, wherein the diluted deep sea water is 2-6% (v/v) diluted deep sea water.

2. The method for cultivating coffee bean tree of claim 1, wherein the irrigation is performed with 2- to 4-day intervals.

* * * * *